(12) United States Patent
Zhang et al.

(10) Patent No.: US 7,091,374 B1
(45) Date of Patent: Aug. 15, 2006

(54) FLUORINATED COMPOUNDS

(75) Inventors: Yuehua Zhang, Mill Creek, WA (US); Manjari Lal, Bellevue, WA (US); Andrew Leo, Kirkland, WA (US); Nagesh Palepu, Mill Creek, WA (US)

(73) Assignee: Sonus Pharmaceuticals, Inc., Bothell, WA (US)

( * ) Notice: Subject to any disclaimer, the term of this patent is extended or adjusted under 35 U.S.C. 154(b) by 59 days.

(21) Appl. No.: 10/830,751

(22) Filed: Apr. 23, 2004

Related U.S. Application Data

(62) Division of application No. 10/300,676, filed on Nov. 20, 2002, now Pat. No. 6,864,386.

(60) Provisional application No. 60/332,020, filed on Nov. 21, 2001.

(51) Int. Cl.
*C07C 231/00* (2006.01)

(52) U.S. Cl. ....................... 560/129; 564/156; 564/160; 568/681; 568/683

(58) Field of Classification Search ................ 564/156, 564/160; 560/129; 568/681, 683
See application file for complete search history.

(56) References Cited

U.S. PATENT DOCUMENTS

| | | | |
|---|---|---|---|
| 3,989,843 A | 11/1976 | Chabert et al. | |
| 4,110,474 A | 8/1978 | Lagow et al. | |
| 4,187,252 A | 2/1980 | Lagow et al. | |
| 4,975,468 A | 12/1990 | Yiv | |

OTHER PUBLICATIONS

Chem. Abstr. of JP-05/289126, 1992.*
Wesseler, E.P., et al., "The Solubility of Oxygen in Highly Fluorinated Liquids," *Journal of Fluorine Chemistry* 9:137-146, 1977.

* cited by examiner

*Primary Examiner*—Deborah D Carr
(74) *Attorney, Agent, or Firm*—Christensen O'Connor Johnson Kindness PLLC

(57) ABSTRACT

Fluorinated compounds and emulsions including the compounds. The compositions are useful as oxygen carriers and surfactants. In one embodiment, the fluorinated compound is pH sensitive. In one embodiment, the fluorinated compound is a vitamin E derivative. In one embodiment, the fluorinated compound is a vitamin K derivative.

8 Claims, 4 Drawing Sheets

$$C_nF_{2n+1}\; C(R)_2 - O - A - O - (B-O)_m - R^1$$

FLUORINATED COMPOUNDS

CROSS-REFERENCES TO RELATED APPLICATIONS

This application is a divisional of U.S. patent application Ser. No. 10/300,676, filed Nov. 20, 2002, which now U.S. Pat. No. 6,864,386, claims the benefit of U.S. Provisional Patent Application No. 60/332,020, filed Nov. 21, 2001, each of which is incorporated herein by reference in its entirety.

FIELD OF THE INVENTION

The present invention relates in general to compounds that fluorinated compounds and, more particularly, to fluorinated compounds that are oxygen carriers.

BACKGROUND OF THE INVENTION

Perfluorocarbon (PFC) emulsions have been utilized in blood substitutes and other medical applications. Emulsion formulations typically include one or more surfactants.

For use in medical applications, an emulsion ideally possesses stability sufficient for storage for long periods of time, for example, for up to several months or even years, at acceptable temperature, preferably room temperature. An emulsion's stability depends on the specific surfactant or surfactants in the emulsion formulation. In medical applications, an emulsion formulation should include emulsion particles that are sufficiently small to pass through the smallest capillaries without creating an obstruction. Emulsion particle size should be less than about 200 nm and not more than about 500 nm. The emulsion formulation should have low toxicity or be non-toxic. The emulsion should be biocompatible, and avoid hemolysis and crenation to red blood cells.

Despite the advances in using perfluorocarbon emulsions as blood substitutes and in other medical applications, there exists a need for perfluorocarbon emulsions having improved properties and a need for surfactants that impart improved properties to such emulsions. The present invention seeks to fulfill this need and provides further related advantages.

SUMMARY OF THE INVENTION

In one aspect, the present invention provides fluorinated compounds that act as surfactants. The fluorinated compounds of the invention have emulsifying and non-toxic properties and can be utilized as oxygen carriers in blood substitutes and other medical applications. In one embodiment, the fluorinated compound is a pH-sensitive compound. In another embodiment, the fluorinated compound is a vitamin E derivative. In a further embodiment, the fluorinated compound is a vitamin K derivative.

In other aspects of the invention, emulsions including the fluorinated compounds, and methods for making the fluorinated compounds are described.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
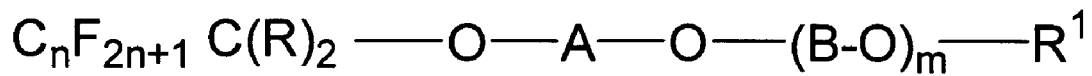
FIG. 1 illustrates the chemical structure of a representative class of fluorinated compounds of the invention.

In one aspect, the present invention provides fluorinated compounds. The fluorinated compounds are surfactants and oxygen carriers. In one embodiment, the invention provides fluorinated compounds that are pH sensitive. In another embodiment, the invention provides fluorinated compounds that are vitamin E derivatives. In a further embodiment, the invention provides fluorinated compounds that are vitamin K derivatives.

In another aspect of the invention, formulations that include the fluorinated compounds are provided. Representative formulations include emulsions and microemulsions.

As used herein, the following terms have the meanings defined below:

The term "vitamin E" refers to a compound that is a member of the tocopherol family. Tocopherols are a family of natural and synthetic compounds, also known by the generic names tocols or vitamin E. α-Tocopherol is the most abundant form of this class of compounds. Other members of this class include α-, β-, γ-, and δ-tocotrienols. Tocopherols also include α-tocopherol derivatives, such as tocopherol acetate, phosphate, succinate, nicotinate, and linoleate.

The term "vitamin K" refers to a member of the vitamin K family that can be incorporated into the fluorinated compounds of the invention. A preferred vitamin K is vitamin K5.

The term "surfactant" refers to a surface active group of an amphiphilic molecule that is manufactured by chemical processes or purified from natural sources or processes. These can be anionic, cationic, nonionic, and zwitterionic. Typical surfactants are described in Emulsions: Paul Becher, *Theory and Practice*, Robert E. Krieger Publishing, Malabar, Fla., 1965; *Pharmaceutical Dosage Forms: Dispersed Systems* Vol. 1, Surfactants, Martin M. Rigear, and U.S. Pat. No. 5,595,723. Each of these references is incorporated herein by reference in its entirety.

The term "emulsion" refers to a colloidal dispersion of two immiscible liquids in the form of droplets, whose diameter, in general, are between 0.1 and 3.0 microns. An emulsion is typically optically opaque, unless the dispersed and continuous phases are refractive index matched. Such systems possess a finite stability, generally defined by the application or relevant reference system, which may be enhanced by the addition of amphiphilic molecules or viscosity enhancers.

The term "microemulsion" refers to a thermodynamically stable isotropically clear dispersion of two immiscible liquids, such as oil and water, stabilized by an interfacial film of surfactant molecules. A microemulsion has a mean droplet diameter of less than about 200 nm, typically between from about 10 to about 50 nm.

As noted above, in one aspect of the invention relates to formulations that include fluorinated a compound. While the formulation of the inventions are referred to herein as emulsions, it should be understood that they may be considered solutions, micellar solutions, microemulsions, vesicular suspensions, or mixtures of one or more of these physical states. Accordingly, the term "emulsion" refers to these states and the fluorinated compounds of the invention can be used to enhance stable mixtures of these states.

For intravenous use, the fluorinated compounds can be dispersed as emulsions in water. See, for example, Clark, L. C., Jr., et al., *Fed. Proc.* 34(6):1468–77, 1975; Yokoyama, K., et al., *Artif. Organs (Cleve)* 8(1):34–40; 1984; and U.S. Pat. Nos. 4,110,474 and 4,187,252. Neat, highly fluorinated organic compounds are immiscible in blood.

In one aspect, the invention provides fluorinated compounds. The compounds have oxygen-carrying and/or surfactant activities. Representative embodiments of fluorinated compounds of the invention are described in Examples 1–5. The fluorinated compounds of the invention can dissolve and transport oxygen. These properties make them useful in various medical applications. For example, the compounds are useful as contrast media for various biological imaging modalities, including nuclear magnetic resonance, $^{19}$F-magnetic resonance imaging, ultrasound, x-ray, and computed tomography. The compounds are also useful as oxygen transport agents or "artificial bloods" which can be advantageously administered in the treatment of heart attack, stroke, and other vascular obstructions, or as adjuvants to coronary angioplasty, and in cancer radiation and chemotherapy.

The fluorinated compounds of the invention also exhibit advantageous surfactant activity. These compounds are physiologically acceptable and, by virtue of their oxygen-carrying properties, obviate the need for adding exogenous surfactants to form emulsions suitable for oxygen transport and delivery.

In one embodiment, the invention provides a compound having the structure:

$$C_nF_{2n+1}—C(R)_2—O—A—O—(B—O)_m—R^1$$

where n=4–12; where m=5–20, where R is at least one of hydrogen, C1–C6 alkyl, or C1–C6 perfluoroalkyl; where A is a polar moiety, as described below; where B—O is at least one of an oxyethylene group or an oxypropylene group (i.e., B is CH$_2$CH$_2$ or CH$_2$CH$_2$CH$_2$); and where R$^1$ is at least one of hydrogen, methyl, a succinic acid moiety (—C(=O) CH$_2$CH$_2$CO$_2$H), or an amino acid moiety.

In another embodiment, the invention provides a compound having the structure:

$$C_nF_{2n+1}—C(R)_2—O—(B—O)_m—R^1$$

where n=4–12; where m=5–20, where R is at least one of hydrogen, C1–C6 alkyl, or C1–C6 perfluoroalkyl; where B—O is at least one of an oxyethylene group or an oxypropylene group; and where R$^1$ is at least one of hydrogen, methyl, a succinic acid moiety, or an amino acid moiety.

In a further embodiment, the invention provides a compound having the structure:

$$C_nF_{2n+1}—C(R)_2—O—A—O—R^2$$

where n=4–12; where m=5–20, where R is at least one of hydrogen, C1–C6 alkyl, or C1–C6 perfluoroalkyl; wherein A is a polar moiety, as described below; and wherein R$^2$ is a hydrophobic moiety. Suitable hydrophobic moieties include vitamin E moieties and vitamin K moieties. In one embodiment, the hydrophobic moiety is an α-tocopherol moiety. In another embodiment, the hydrophobic moiety is a vitamin K5 moiety. Other suitable hydrophobic moieties include long and medium chain length alcohol and fatty acid moieties.

For these embodiments, polar moiety A can be one of the following moieties:
—CH$_2$CH(OH)CH$_2$—;
—CH$_2$CH(O(C=O)CH$_2$CH$_2$CO$_2$H)CH$_2$—;
—C(=O)(CH$_2$)$_2$C(=O)—;
—C(=O)NH(CH$_2$)$_4$NHC(=O)—;
—C(=O)NH(CH$_2$)$_6$NHC(=O)—; or
—C(=O)NH—C$_6$H$_4$—NHC(=O)—, where C$_6$H$_4$ refers to a disubstituted benzene, for example, para- or meta-disubstituted benzene.

For the above compounds, "alkyl" refers to suitable alkyl groups including, for example, cyclic, branched, and unbranched C1–C6 alkyl groups, such as methyl, ethyl, propyl, butyl, pentyl, and hexyl groups; and "perfluoroalkyl" refers to suitable perfluoroalkyl groups including, for example, cyclic, branched, and unbranched C1–C6 alkyl groups, such as methyl, ethyl, propyl, butyl, pentyl, and hexyl groups.

For embodiments that include amino acid moieties, suitable amino acid moieties include alanine, arginine, glutamine, glutamic acid, glycine, lysine, and valine moieties.

The fluorinated compounds of the invention include those illustrated schematically in FIGS. 1–6. Referring to FIG. 1, in one embodiment, the fluorinated compound includes a fluorinated first region (C$_n$F$_{2n+1}$—C(R$_2$)—), a second region (A) including one or more polar groups (e.g., carboxyl, ester, amide, alcohol, amine), a third region (B—O) including a polyoxyethylene group and/or a polyoxypropylene group, and a fourth region (R$^1$) that can include a pH-sensitive group (i.e., an acidic or basic group), such as a carboxylic acid group or amino acid group.

Figure 2:
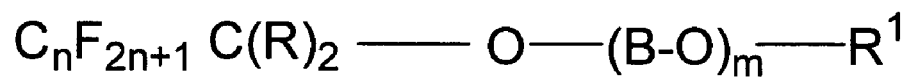
FIG. 2 illustrates the chemical structure of a second representative class of fluorinated compounds of the invention.

Referring to FIG. 2, in another embodiment, the fluorinated compound includes a fluorinated first region (C$_n$F$_{2n+1}$—C(R$_2$)—), a second region (B—O) including a polyoxyethylene group and/or a polyoxypropylene group, and a third region (R$^1$) that can include a pH-sensitive group (i.e., an acidic or basic group), such as a carboxylic acid group or amino acid group.

Figure 3:
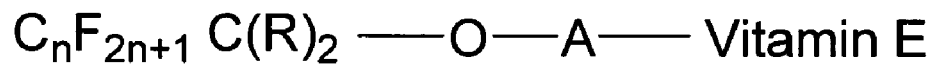
FIG. 3 illustrates the chemical structure of a third representative class of fluorinated compounds of the invention.
Figure 5:
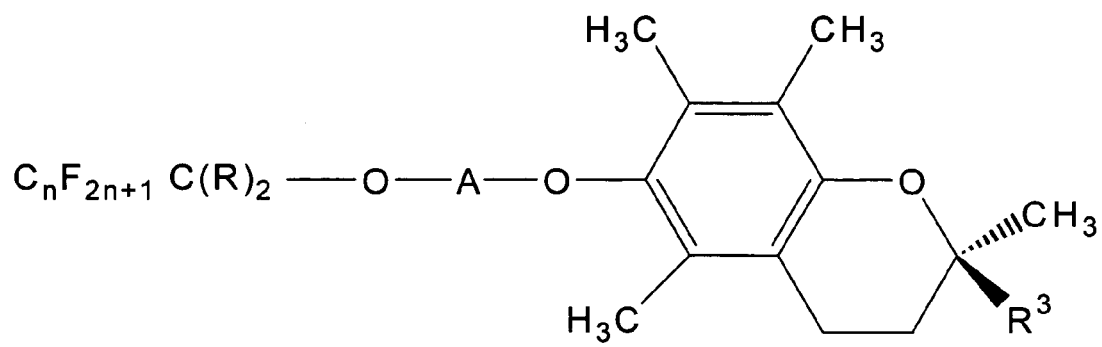
FIG. 5 illustrates the chemical structure of a representative class of vitamin E fluorinated compounds of the invention.
Figure 5:
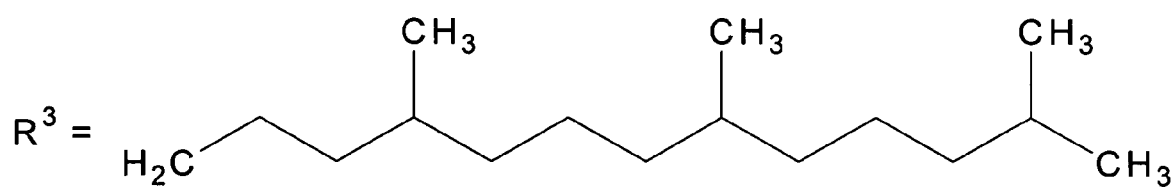

Referring to FIG. 3, in another embodiment, the fluorinated compound includes a fluorinated first region (C$_n$F$_{2n+1}$—C(R$_2$)—), a second region (A) including one or more polar groups (e.g., carboxyl, ester, amide, alcohol, amine), and a third region that includes a vitamin E moiety. FIG. 5 illustrates a fluorinated compound that includes a vitamin E (i.e., α-tocopherol) moiety.

Figure 4:
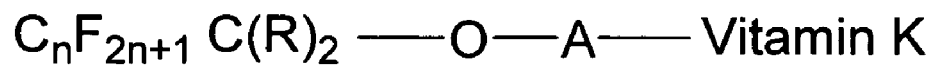
FIG. 4 illustrates the chemical structure of a fourth representative class of fluorinated compounds of the invention.
Figure 6:
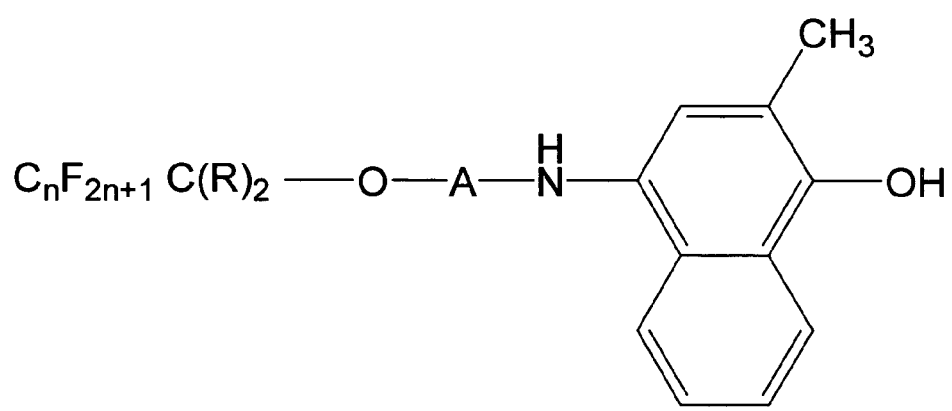
FIG. 6 illustrates the chemical structure of a representative class of vitamin K fluorinated compounds of the invention.

Referring to FIG. 4, in another embodiment, the fluorinated compound includes a fluorinated first region (C$_n$F$_{2n+1}$—C(R$_2$)—), a second region (A) including one or more polar groups (e.g., carboxyl, ester, amide, alcohol, amine), and a third region that includes a vitamin K moiety. FIG. 6 illustrates a fluorinated compound that includes a vitamin K (i.e., vitamin K5) moiety.

In FIGS. 1–6, n=4–12; and in FIGS. 1 and 2, m=5–20.

In one embodiment, the invention provides pH-sensitive fluorinated compounds that are surfactants and that provide a pH dependent sustained release system for oxygen delivery. A representative pH-sensitive fluorinated compound is described in Example 3. These fluorinated compounds can include one or more protonatable polar groups, such as a carboxyl group ($-CO_2H$) that can form strong hydrogen bonding at low pH (about pH 3 to about pH 5). In these embodiments, the compound is relatively less amphiphilic at lower pH and becomes more emulsifying at higher pH (about pH 6 to about pH 7).

The strong hydrogen bonding of such pH-sensitive fluorinated compounds can result in the formation of a stable shell on the surface of micelles. The shell will tightly hold the micelle to prevent micelle aggregation thereby controlling micelle particle size. The formation of hydrogen bonds at low pH also assists in solubilizing and stabilizing a perfluorocarbon gas (for example, dodecafluoropentane, DDFP) that can be contained within the micelle at low pH, and released from the micelle at higher pH (about pH 6 to about pH 7).

In another aspect of the invention, formulations that include a fluorinated compound having oxygen-carrying and/or emulsifying activities are provided. Such formulations include physiologically acceptable emulsions.

The formulations of the invention include one or more of the fluorinated compounds of the invention. In addition to the fluorinated compounds of the invention, the formulations can include other components conventionally used in "artificial bloods" or blood substitutes, oxygen transport agents, or contrast media. For example, formulations according to this invention usually also contain an isotonic agent, typically sugars, such as glucose, mannose and fructose, glycerin, or other polyhydric alcohols to adjust the osmotic pressure of the formulation to about that of blood. Osmolarity may also be adjusted after sterilization by buffers such as sodium chloride, sodium bicarbonate, magnesium chloride, and the like, to reduce the possibility of red blood cell injury. In addition, these formulations may be mixed with 0.9 percent saline, lactated Ringer's solution, and serum and serum products that have no adverse effect on emulsion particle size and stability. The formulations of this invention may also include osmotic agents, for example, dextran or hydroxyethylstarch (HES). Other physiologically acceptable additives may be included in the formulations, such as acidifying, alkalizing, buffering, chelating, complexing and solubilizing agents, antioxidants and antimicrobial preservatives, humectants, suspending and/or viscosity modifying agents, tonicity and wetting or other biocompatible materials known in the art.

Methods for making representative fluorinated compounds of the invention having oxygen-carrying and surfactant activities are described in Examples 1–5.

The following examples are provided for the purpose of illustrating, not limiting, the invention.

EXAMPLES

Example 1

The Preparation of a Representative Fluorinated Compound: $CF_3(CF_2)_7C(CF_3)_2O-CH_2CH(OH)CH_2O-(CH_2CH_2O)_nH$ In this example, the preparation of a representative fluorinated alcohol of the invention, $CF_3(CF_2)_7C(CF_3)_2O-CH_2CH(OH)CH_2-O-(CH_2CH_2O)_nH$, is described. For this compound, n is 6.

To a 50 ml flask containing 10 ml tetrahydrofuran was added 10.00 g 2-trifluoromethyl perfluorodecan-2-ol, $CF_3(CF_2)_7C(CF_3)_2OH$ (Synquest), and 1.36 g 50% aqueous sodium hydroxide. The mixture was stirred at room temperature for 1 hour. The tetrahydrofuran and water were removed by reduced pressure, and the resulting product dried in vacuo to provide the alcohol sodium salt as white powder.

The alcohol sodium salt was dissolved in 20 ml tetrahydrofuran in a 100 ml flask. To this solution was added 2.34 g epibromohydrin (Sigma) in 10 ml of tetrahydrofuran, and the mixture was stirred at 65° C. overnight. The mixture was cooled to room temperature and concentrated to dryness. The residue was dissolved in ether and the resulting mixture was filtered to remove sodium bromide. The ether was then removed to provide 2,3-epoxypropyl-2-trifluoromethylperfluorodecan ether.

Figure 7:
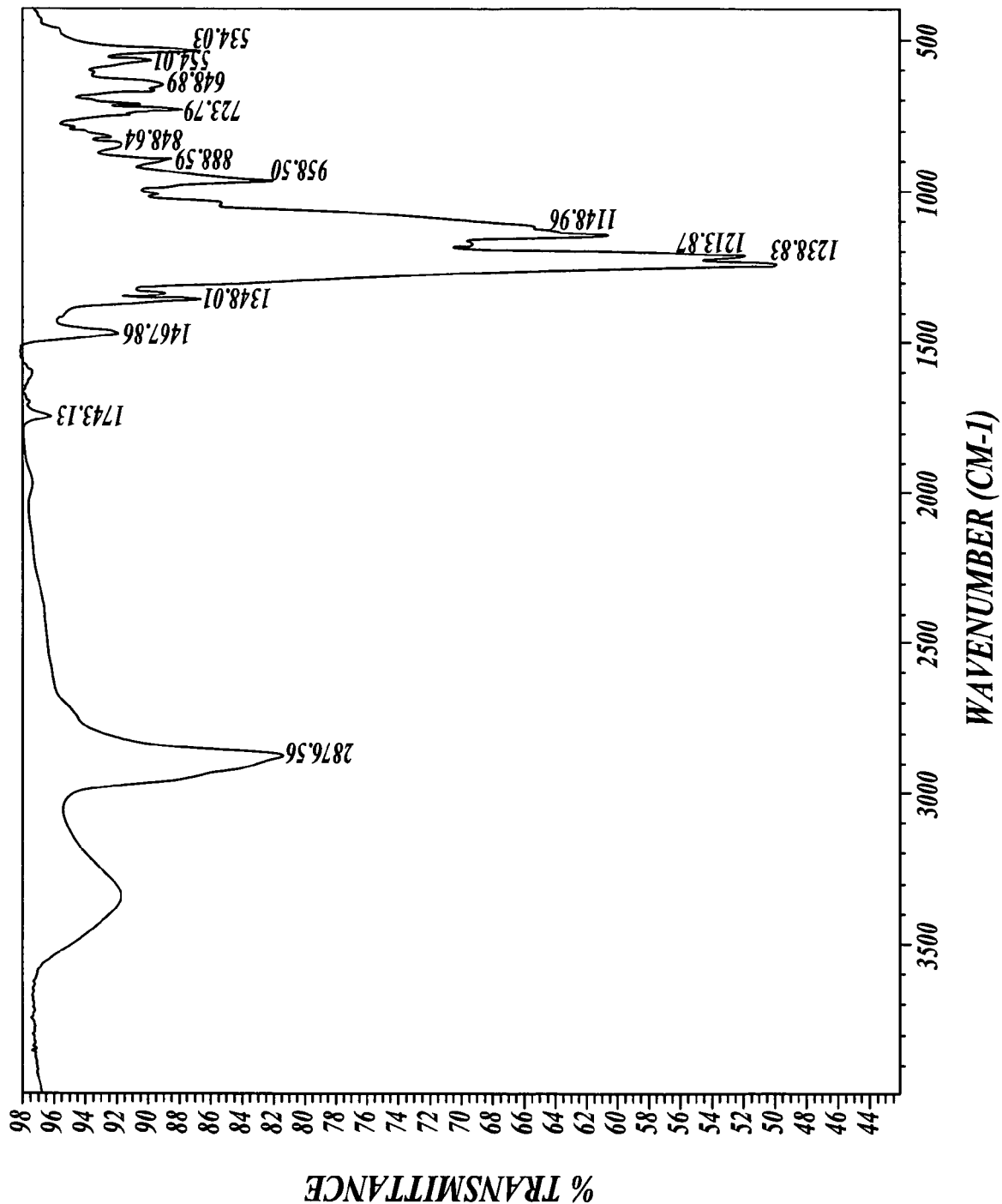
FIG. 7 is an infrared absorption spectrum of a representative fluorinated compound of the invention.

A mixture of 6.82 g polyethylene glycol (300 grams/mole) and 0.95 g potassium hydroxide was stirred under nitrogen at 100° C. for 1 hour such that potassium hydroxide was dissolved. To the mixture was added the 2,3-epoxypropyl-2-trifluoromethylperfluorodecan ether in 10 ml tetrahydrofuran. The mixture was stirred under nitrogen at 100° C. for two hours, cooled to room temperature, and then 0.5 g water was added to the mixture. The mixture was stirred for an additional 30 minutes. The solvent and water were then removed by vacuum. The residue was dissolved in diethyl ether and the resulting mixture filtered. The filtrate was concentrated to dryness to the yield the product, as an oil (83%). The infrared spectrum of the product is shown in FIG. 7.

Example 2

The Preparation of a Representative Fluorinated Compound: $CF_3(CF_2)_7C(CF_3)_2O-CONH(CH_2)_4NHCO-O-(CH_2CH_2O)_nCH_3$ In this example, the preparation of a representative fluorinated compound of the invention, $CF_3(CF_2)_7C(CF_3)_2O-CONH(CH_2)_4NHCO-O-(CH_2CH_2O)_nCH_3$, is described. For this compound, n is 12.

To a 50 ml flask was added 10 ml tetrahydrofuran, 2.00 g 2-trifluoromethylperfluorodecan-2-ol, $CF_3(CF_2)_7C(CF_3)_2OH$ (Synquest), 2.4 g 1,4-diisocyanatobutane, and 10 mg tin (II) 2-ethylhexanoate. The mixture was stirred at 65° C. for 2 hours. Tetrahydrofuran and excess 1,4-diisocyanatobutane were removed by vacuum. The residue was then dissolved in 10 ml tetrahydrofuran and 1.88 g polyethylene glycol methyl ether (550 grams/mole) was added. The mixture was stirred at room temperature overnight. The tetrahydrofuran was removed under vacuum and the residue extracted three times with hexane. The product was obtained by concentration of the hexane solution to yield the product, as an oil (90%).

Example 3

The Preparation of a Representative Fluorinated Compound: $CF_3(CF_2)_7C(CF_3)_2O\text{—}CH_2CH(OH)CH_2\text{—}O\text{—}(CH_2CH_2O)_n\text{—}COCH_2CH_2CO_2H$ In this example, the preparation of a representative pH sensitive fluorinated compound of the invention, $CF_3(CF_2)_7C(CF_3)_2O\text{—}CH_2CH(OH)CH_2\text{—}O\text{—}(CH_2CH_2O)_n\text{—}COCH_2CH_2CO_2H$, is described. For this compound, n is 6.

Figure 8:
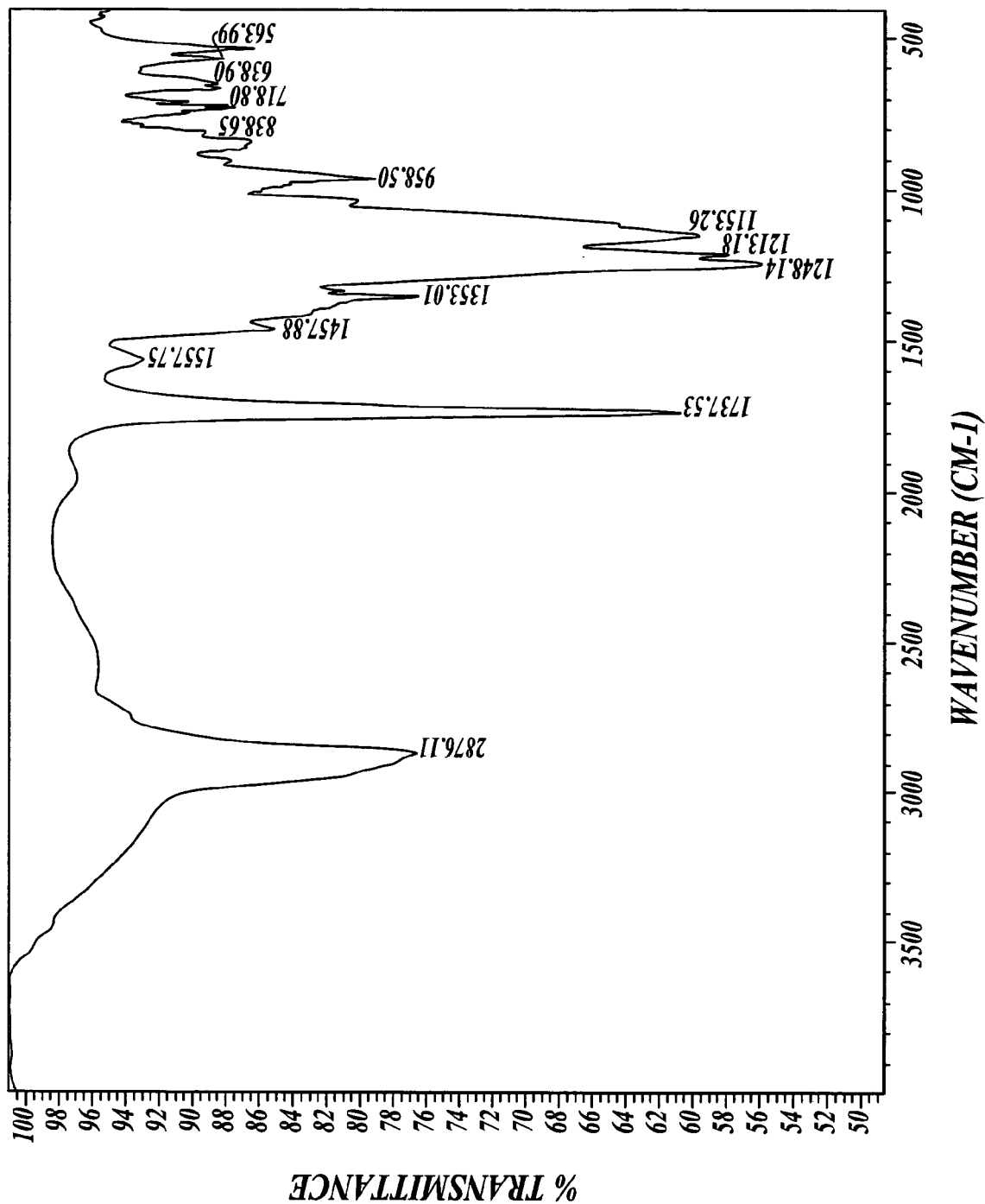
FIG. 8 is an infrared absorption spectrum of a representative fluorinated compound of the invention.

To a 50 ml flask was added 0.74 g succinic anhydride, 50 mg tin (II) ethyl hexanoate, and 14.3 g of the fluorinated compound prepared as described in Example 1 above. The mixture was heated to 140° C. under nitrogen for 4 hours to yield the product, as a yellowish oil (95%). The infrared spectrum of the product is shown in FIG. 8.

Example 4

The Preparation of a Representative Fluorinated Compound: $CF_3(CF_2)_7C(CF_3)_2O\text{—}CONH(CH_2)_4NHCO\text{-Vitamin E}$ In this example, the preparation of a representative fluorinated vitamin E compound of the invention, $CF_3(CF_2)_7C(CF_3)_2O\text{—}CONH(CH_2)_4NHCO\text{-Vitamin E}$, is described. The structure of this compound is illustrated in FIG. 5, where A is $CONH(CH_2)_4NHCO$, R is $CF_3$, and n=8.

To a 50 ml flask was added 10 ml tetrahydrofuran, 2.00 g 2-trifluoromethylperfluorodecan-2-ol, $CF_3(CF_2)_7C(CF_3)_2OH$ (Synquest), 2.4 g 1,4-diisocyanatobutane, and 10 mg tin (II) 2-ethylhexanoate. The mixture was stirred at 65° C. for 2 hours. Tetrahydrofuran and excess 1,4-diisocyanatobutane were removed by vacuum. The residue was then dissolved in 10 ml tetrahydrofuran and 1.47 g vitamin E was added. The mixture was stirred at room temperature overnight. The tetrahydrofuran was removed under vacuum, and residue was extracted three times with hexane. The product was obtained by concentration of the hexane solution to yield the product.

Example 5

The Preparation of a Representative Fluorinated Compound: $CF_3(CF_2)_7C(CF_3)_2O\text{—}CONH(CH_2)_4NHCO\text{-Vitamin K5}$ In this example, the preparation of a representative fluorinated vitamin K compound of the invention, $CF_3(CF_2)_7C(CF_3)_2O\text{—}CONH(CH_2)_4NHCO\text{-Vitamin K5}$, is described. The structure of this compound is illustrated in FIG. 6, where A is $CONH(CH_2)_4NHCO$, R is $CF_3$, and n=8.

To a 50 ml flask is added 10 ml tetrahydrofuran, 2.00 g 2-trifluoromethylperfluorodecan-2-ol, $CF_3(CF_2)_7C(CF_3)_2OH$ (Synquest), 2.4 g 1,4-diisocyanatobutane, and 10 mg tin (II) 2-ethylhexanoate. The mixture is stirred at 65° C. for 2 hours. Tetrahydrofuran and excess 1,4-diisocyanatobutane are removed by vacuum. The product is then dissolved in 10 ml tetrahydrofuran and 1.47 g vitamin K5 is added. The mixture is stirred at room temperature overnight. The tetrahydrofuran is removed under vacuum, and residue is extracted three times with hexane. The product is obtained by concentration of the hexane solution to yield the product.

While the preferred embodiment of the invention has been illustrated and described, it will be appreciated that various changes can be made therein without departing from the spirit and scope of the invention.

The invention claimed is:

1. A compound having the structure:

$$C_nF_{2n+1}\text{—}C(R)_2\text{—}O\text{—}A\text{—}O\text{—}R^2$$

wherein n=4–12; wherein m=5–20, wherein each R is independently hydrogen, C1–C6 alkyl, or C1–C6 perfluoralkyl; wherein $R^2$ is a vitamin E moiety, a vitamin K moiety, a fatty alcohol moiety, or a fatty acid moiety; and wherein A is
—$CH_2CH(OH)CH$—,
—$CH_2CH(O(C=O)CH_2CH_2CO_2H)CH_2$—,
—$C(=O)(CH_2)_2C(=O)$—,
—$C(=O)NH(CH_2)_4NHC(=O)$—,
—$C(=O)NH(CH_2)_6NHC(=O)$—, or
—$C(=O)NH\text{—}C_6H_4\text{—}NHC(=O)$—.

2. The compound of claim 1, wherein R is $CF_3$.

3. The compound of claim 1, wherein n is 8.

4. The compound of claim 1, wherein $R^2$ is a vitamin E moiety.

5. The compound of claim 1, wherein $R^2$ is a vitamin K moiety.

6. The compound, $CF_3(CF_2)_7C(CF_3)_2O\text{—}CONH(CH_2)_4NHCO\text{-Vitamin E}$.

7. The compound, $CF_3(CF_2)_7C(CF_3)_2O\text{—}CONH(CH_2)_4NHCO\text{-Vitamin K5}$.

8. An emulsion, comprising the compound of claim 1.

* * * * *

UNITED STATES PATENT AND TRADEMARK OFFICE
CERTIFICATE OF CORRECTION

PATENT NO. : 7,091,374 B1  Page 1 of 1
APPLICATION NO. : 10/830751
DATED : August 15, 2006
INVENTOR(S) : Y. Zhang et al.

It is certified that error appears in the above-identified patent and that said Letters Patent is hereby corrected as shown below:

| | | |
|---|---|---|
| On The Title Page | (Primary Examiner) | "Deborah D Carr" should read --Deborah D. Carr-- |
| Col. 8 | line 30 | "–$CH_2CH(OH)CH\_$," should read -- –$CH_2CH(OH)CH_2$–, -- |
| Col. 8 (Claim 9) | line 48 | after "8. An emulsion, comprising the compound of claim 1." insert new paragraph --9. An emulsion, comprising the compound of Claim 4.-- |
| Col. 8 (Claim 10) | line 30 | after "8. An emulsion, comprising the compound of claim 1." and "9. An emulsion, comprising the compound of Claim 4." insert --10. An emulsion, comprising the compound of claim 5.-- |

Signed and Sealed this

Sixteenth Day of October, 2007

JON W. DUDAS
*Director of the United States Patent and Trademark Office*